US006883963B2

United States Patent
Nolewaika

(10) Patent No.: US 6,883,963 B2
(45) Date of Patent: Apr. 26, 2005

(54) METHOD FOR EXCHANGING DETECTOR MODULES IN AN X-RAY DETECTOR IN A COMPUTED TOMOGRAPH

(75) Inventor: Stefan Nolewaika, Neustadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/615,029

(22) Filed: Jul. 9, 2003

(65) Prior Publication Data

US 2004/0135091 A1 Jul. 15, 2004

(30) Foreign Application Priority Data

Jul. 9, 2002 (DE) ......................................... 102 31 024

(51) Int. Cl.$^7$ ........................... G01D 18/00; H05G 1/64
(52) U.S. Cl. ...................... 378/207; 378/19; 250/252.1; 250/370.09; 250/370.15
(58) Field of Search ..................... 378/19, 98.8, 207; 250/252.1, 370.09, 370.15

(56) References Cited

U.S. PATENT DOCUMENTS

| | | | | |
|---|---|---|---|---|
| 5,970,113 A | * | 10/1999 | Crawford et al. | ............. 378/19 |
| 6,396,898 B1 | * | 5/2002 | Saito et al. | .................... 378/19 |
| 6,411,673 B1 | | 6/2002 | Bromberg et al. | ............. 378/19 |
| 6,453,008 B1 | * | 9/2002 | Sakaguchi et al. | ......... 378/98.7 |
| 6,651,018 B1 | | 11/2003 | Kropfeld et al. | .............. 702/85 |
| 6,667,482 B1 | * | 12/2003 | Von Der Haar | ........ 250/370.11 |
| 2004/0190683 A1 | * | 9/2004 | Winklemann | ................ 378/207 |

FOREIGN PATENT DOCUMENTS

| DE | 101 12 792 | 3/2001 |
|---|---|---|
| DE | 101 38 922 | 8/2001 |
| DE | 101 64 281 | 12/2001 |

* cited by examiner

*Primary Examiner*—Allen C. Ho
(74) *Attorney, Agent, or Firm*—Harness, Dickey & Pierce, P.L.C.

(57) ABSTRACT

A method is for exchanging a first detector module (m), in an X-ray detector in a computed tomograph having a module configuration a, for a second detector module (m'). The first detector module has an associated correction table ($T_{S(a,m,x)}$) for eliminating temperature-dependent signal changes, which is dependent on the respective module configuration of the detector and which is recreatable following the exchange of a detector module.

For the first and second detector modules (m, m') in a detector in a reference computed tomograph having the module configuration b, a respective correction table ($T_{S(b,m,x)}$, $T_{S(b,m',x)}$) is created. Differences, preferably only in the area of the channels of the detector module which is to be exchanged, are ascertained. Finally, the new correction table ($T_{S(a,m',x)}$) for operating the second detector module (m') in the computed tomograph having the module configuration a is calculated by transferring the ascertained difference values to the old correction table ($T_{S(a,m,x)}$).

16 Claims, 2 Drawing Sheets

METHOD FOR EXCHANGING DETECTOR MODULES IN AN X-RAY DETECTOR IN A COMPUTED TOMOGRAPH

The present application hereby claims priority under 35 U.S.C. §119 on German patent application number DE 10231024.6 filed Jul. 9, 2002, the entire contents of which are hereby incorporated herein by reference.

FIELD OF THE INVENTION

The invention generally relates to a method for exchanging a first detector module m, having K channels from k to j in an X-ray detector in a computed tomograph having a module configuration a with a total of M detector modules and K×M channels, for a second detector module m'. The first detector module preferably has an associated correction table $T_{S(a,m,x)}$ for eliminating temperature-dependent signal changes, which is dependent on the respective module configuration of the detector and needs to be recreated following the exchange of a detector module.

BACKGROUND OF THE INVENTION

It is general knowledge that the individual detector elements which are contained in the detector modules of a computed tomograph and supply the detector module's channels with signals have temperature-dependent signal errors which are corrected using correction tables stored in the computed tomograph's processor. Such a correction table uses the differential changes in a detector's channel signals for a respectively prescribed configuration of the detector modules in the detector.

Creating this correction table requires a high level of involvement. Further, it is created in the factory upon the delivery of a computed tomograph for the detector with its detector modules in the respective configuration which is to be delivered. If a detector module, or usually one or more channels in a detector module, is faulty, it is necessary to exchange this module.

Since each detector module has correction values which are firstly module-typical but are secondly also dependent on the respective module configuration, that is to say on a detector module additionally provided in the detector, it is not simply possible to create such a correction table for each individual detector module away from its surroundings. Instead, it is necessary to create the correction table for the new detector module in relation to the surroundings of the entire detector, more precisely in relation to the surroundings of the other detector modules in the overall detector, that is to say in the respective module configuration.

This currently indicates that exchanging a detector module requires highly qualified personnel with correspondingly complex testing equipment to create such a correction table at the site of the computed tomograph, that is to say generally on the customer's premises. Such a method is complex, time-consuming and correspondingly expensive, particularly "in situ".

SUMMARY OF THE INVENTION

This gives rise to an object of finding a method which permits a detector module to be exchanged, without having to perform the complex procedure of creating a correction table on the customer's installation.

An embodiment of the invention is based on the following ideas:

If the complexity for exchanging the detector module in a CT detector is jointly determined to a significant extent by the creation of a correction table for the temperature-dependent response of this detector module, then one aim should be able to exchange a module at the customer's premises without the need for individual creation of a correction table in situ. In this case, it is possible to revert to measurements which are created under the factory conditions more favorable for testing. As a result, the repair of a detector, which requires a module to be exchanged, should be restricted to the absolute minimum, namely to the mechanical exchange of the detector module and to the subsequent calibration of the computed tomograph. The text below illustrates the theoretical considerations on which the inventive method is based.

The relative, temperature-dependent signal change $S_{a,m,x}$ in the channel x of a detector module m in the surroundings of a module configuration a can be defined as follows:

$$S_{a,m,x} = S_{m,x} - \frac{1}{N}(M_1 + M_2 + \ldots + M_m + \ldots M_N),$$

where $S_{m,x}$ is the absolute value of the signal change, which is independent of the respective module configuration, $M_m$ is the absolute mean of the signal change in the module m, which is dependent on the respective module configuration, and N is the number of detector modules.

Accordingly, for every identical channel x of the module configuration a, following an exchange of module from m to m', the signal change can be described as follows:

$$S_{a,m',x} = S_{m',x} - \frac{1}{N}(M_1 + M_2 + \ldots + M_{m'} + \ldots M_N),$$

where m' is intended to be the index for the now new module m'.

The following is obtained from the difference between the two equations cited above for the modules m and m':

$$S_{a,m',x} - S_{a,m,x} = S_{m',x} - S_{m,x} - \frac{1}{N}(M_{m'} - M_m).$$

For these last two equations, the following relationship is obtained by subtracting the equations:

$$S_{a,m',x} = S_{b,m',x} + (S_{a,m,x} - S_{b,m,x}).$$

This thus indicates that, for each channel, the signal change S in a new detector module m' can be calculated on the customer's premises on the basis of known signal changes in the new module m' in a reference configuration b for the signal changes in the old module m in the customer configuration a and the signal change in the old module in the reference configuration b. If this calculation is carried out for each of the channels, then an overall correction table can be created for a newly exchanged detector module in a customer installation, if the correction tables for the old module are available for the customer's installation and a reference installation. Further, the correction table for the new module is available in the same reference installation.

In practice, however, it is found that a detector module also needs to be exchanged if there is a fault in one of its channels. For this reason, useful information which goes beyond the respective possibly faulty channel is sought.

This can be done using the property of the detector module that the mean of the signal changes behaves independently of the respective module configuration. The following is true:

$$S_{a,m,x} - \frac{1}{K}\sum_{i=k}^{j} S_{a,m,i} = S_{b,m,x} - \frac{1}{K}\sum_{i=k}^{j} S_{b,m,i}$$

In this case, the indices k to j represent the individual channels of the respective module, with the index x specifying a channel between k and j.

Resolving the equation following the signal change $S_{a,m,x}$ in the module m' which is to be newly used in the customer's installation with the module configuration a for the channel x then results in the following formula:

$$S_{a,m,x} = S_{b,m,x} + \frac{1}{K}\left(\sum_{i=k}^{j} S_{a,m,i} - \sum_{i=k}^{j} S_{b,m,i}\right).$$

Since the formula cited above still takes account of the presence of all the channels, it should be pointed out that, when faulty channels in the old module arise, the signal changes $S_{a,m,i}$ and/or $S_{b,m,i}$ in the respective faulty channels can be approximated either through interpolation or extrapolation for the adjacent channels' marginal channels, with the error possibly caused thereby moving in the area of approximately 1/K. Normally, a detector module has up to 16 channels, which indicates that this results in an error of at most approximately 6%. If a plurality of channels in a module fail simultaneously, then this error can increase, and an equalization calculation of this type no longer appears appropriate in the event of damage with, for example, more than four faulty channels.

In line with the basic concept of an embodiment of the invention outlined above, the inventor proposes a method for exchanging a detector module having K channels x from k to j in an X-ray detector in a computed tomograph having a module configuration a with a total of M detector modules and K×M channels for a second detector module m', where the first detector module has an associated correction table $T_{S(a,m,x)}$ for eliminating temperature-dependent signal changes which is dependent on the respective module configuration of the detector and needs to be recreated following the exchange of a detector module. The inventive method provides that for the first and second detector modules m, m', preferably at the same position, in a detector in a reference computed tomograph having the module configuration b, a respective correction table $T_{S(b,m,x)}$, $T_{S(b,m',x)}$ is created and its differences, preferably only in the area of the channels of the detector module which is to be exchanged, are ascertained and the new correction table $T_{S(a,m',x)}$ for operating the second detector module m' in the computed tomograph having the module configuration a is calculated by transferring the ascertained difference values to the old correction table $T_{S(a,m,x)}$.

This currently outlined method now allows exchange of a detector module in a particular computed tomograph preferably in a customer's computed tomograph, without the need to determine a correction table for the new detector module in this computed tomograph by way of measurement in situ.

In one development of this inventive method, the inventor also proposes calculating the individual values for the new correction table $T_{S(a,m,x)}$ according to the following formula:

$$S_{a,m',x} = S_{b,m',x} + \frac{1}{K}\left(\sum_{i=k}^{j} S_{a,m,i} - \sum_{i=k}^{j} S_{b,m,i}\right)$$

where K corresponds to the number of channels in a detector module, where the detector module has the channels k to j—the channels in an X-ray detector are counted continuously and across detectors, $S_{n,o,p}$ corresponds to the correction value S for the module configuration n with the detector module o, and the channel x is an element of channels k to j in this detector module o.

For the case of a detector module m to be exchanged which has a faulty channel i, the inventor also proposes calculating the signal values S for this respective failed channel by interpolating or extrapolating adjacent channels. As such, it is also possible to exchange detector modules which firstly have failed channels and for which, secondly, it has not been possible to perform any previously archived measurement on the reference detector. This indicates that the missing information needs to be provided by way of an appropriate consolidated approximation calculation or estimate.

According to an embodiment of the invention, it is possible to establish whether a channel is regarded as being faulty as a result of, by way of example, the measured signal values for this channel exceeding a prescribed limit value, the method for selecting such a limit value being known per se and being used commonly in practice.

As already illustrated in the fundamental considerations for an embodiment of the invention, the new correction table $T_{S(a,m',x)}$ can be created by reverting to a correction table $T_{S(a,m,x)}$ measurement, that is to say for the old module in the customer installation's module configuration, which was created and archived prior to the failure, preferably before the computed tomograph was delivered.

It can likewise be particularly advantageous to create the new correction table $T_{S(a,m',x)}$ by reverting to a correction table $T_{S(b,m,x)}$ measurement. That is to say, a measured correction table can be created for the old module in a reference installation having the module configuration b at the factory—which was created and archived prior to the failure, preferably before the computed tomograph was delivered.

Additional features and advantages of the invention can be found in the description below of preferred exemplary embodiments with reference to the drawings.

BRIEF DESCRIPTION OF THE DRAWINGS

At least one embodiment of the invention will be explained in more detail below with reference to the drawings, in which.

DETAILED DESCRIPTION OF THE PREFERRED EMBODIMENTS

Figure 1:
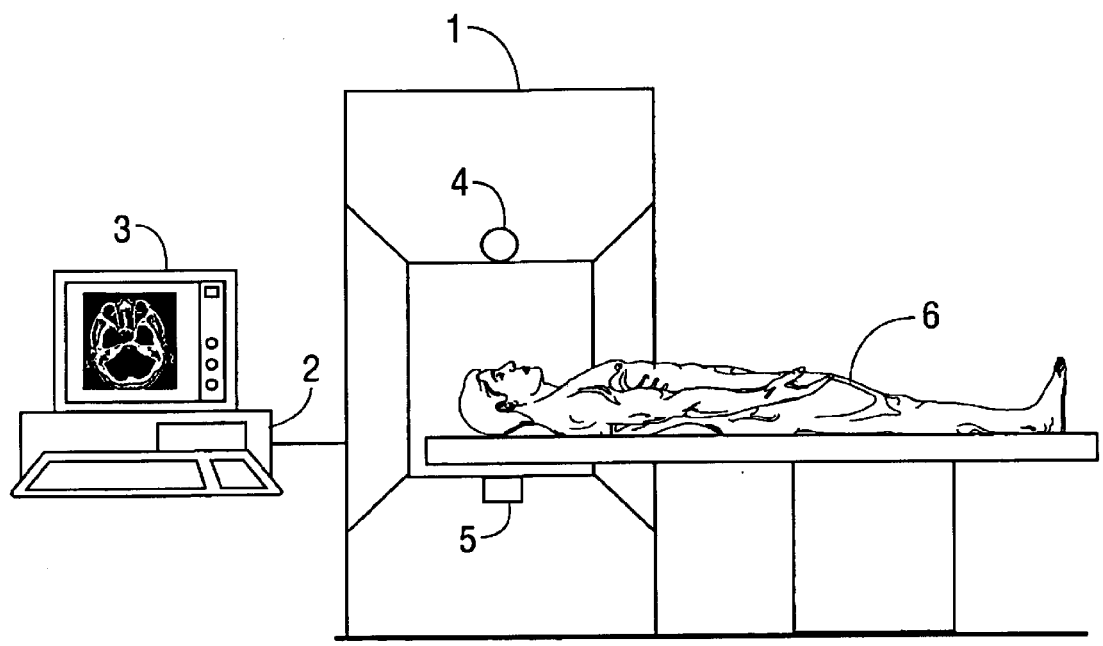
FIG. 1 shows a schematic illustration of a computed tomograph from the side.
Figure 2:
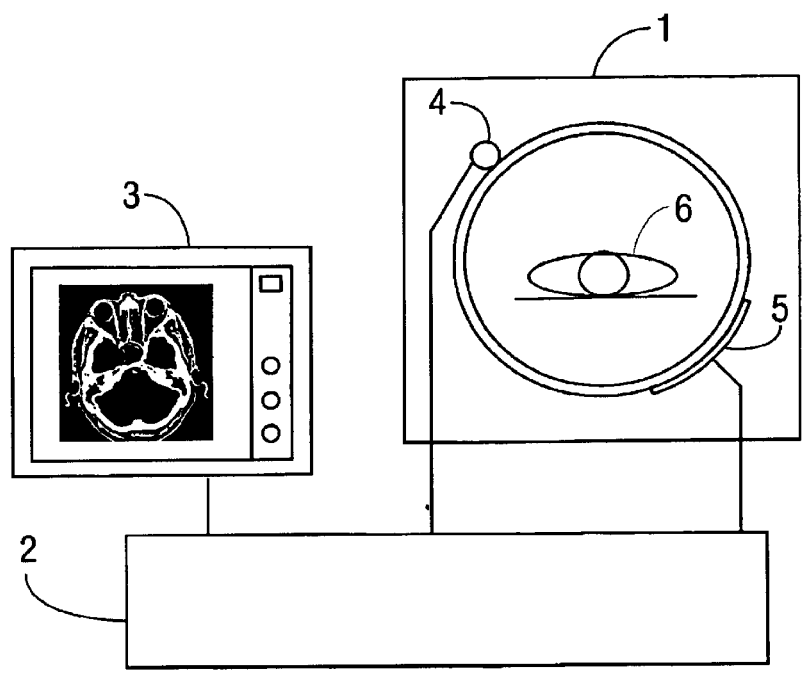
FIG. 2: shows a schematic illustration of a computed tomograph from the front.

FIGS. 1 and 2 show a schematic illustration of a computed tomograph from the side and from the front.

The computed tomography includes a scanning unit 1 which has an X-ray source 4, rotating about a central axis, and a detector 5 between which the object to be examined, in this case a patient 6, is situated. The scanning unit 1 is controlled and the received signals are evaluated by a processor 2 which shows the graphical illustration of one or more virtual sections on a screen 3 as the result of one or more scans.

Figure 3:
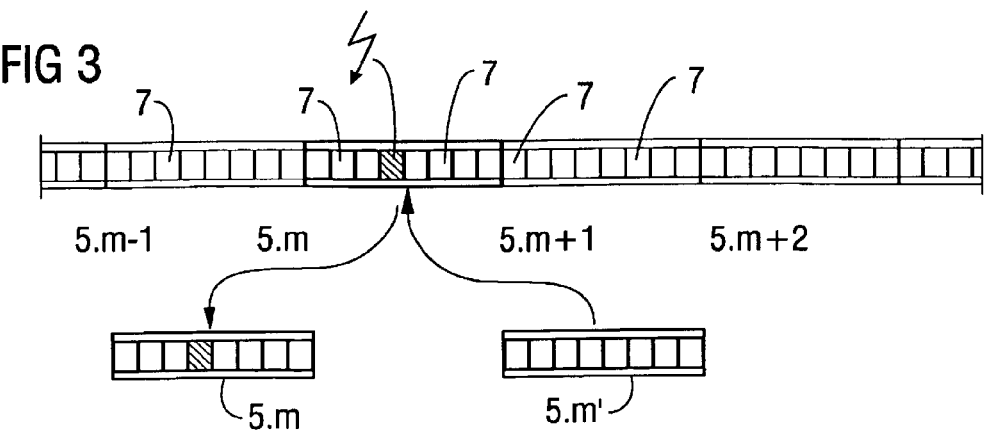
FIG. 3 shows a schematic illustration of a subsection of a detector with detector modules, and exchange thereof.

The detector 5 shown comprises a multiplicity of detector modules in a row which, as shown in FIG. 3, have a multiplicity of detector elements 7 for each detector module 5.*x*, the individual detector elements 7 respectively feeding a channel in the overall detector. FIG. 3 schematically shows the operation of exchanging a detector module 5.*m* for a new detector module 5.*m'*. Each of the detector modules shown schematically in this case has a number of eight detector elements which supply the eight respective channels in these currently shown detector modules with signal information. It should be pointed out that, in reality, such detector modules are usually provided with sixteen channels, but the number of channels per detector module or the number of detector elements per detector module and also the number of detector modules per overall detector are of no significance to the embodiment of the invention.

Figure 4:
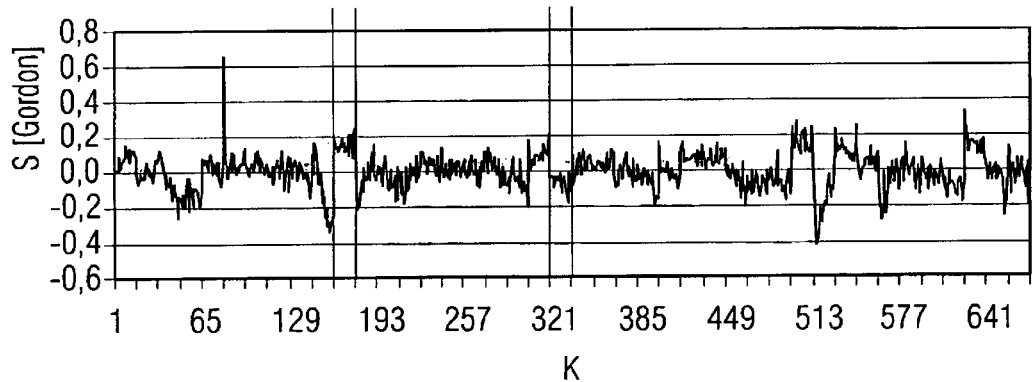
FIG. 4 shows a graphical illustration of the correction table on the basis of measurements.
Figure 5:
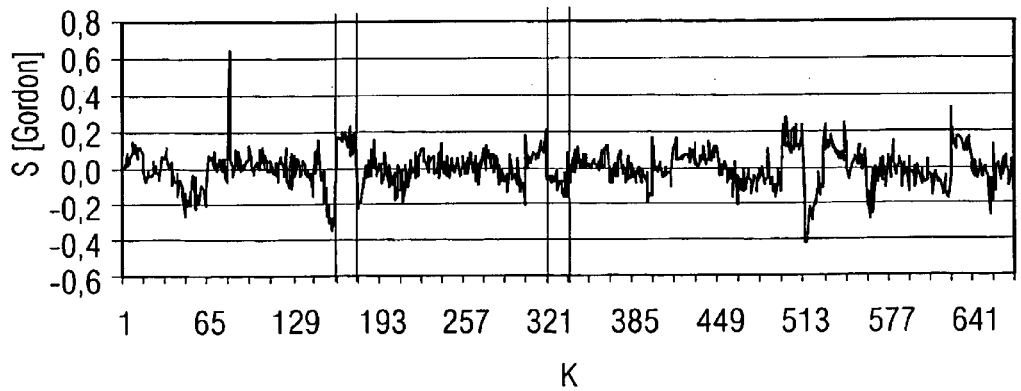
FIG. 5 shows a graphical illustration of the values S in the correction table with calculated values for two modules.

FIGS. 4 and 5 show the signal values S actually measured, indicated in the unit "Gordon", which have been measured for an overall detector having the channels 1 to 672 for a particular module configuration following the exchange of second detector modules in the region between the channels 161 to 176 and 321 to 336.

The cited unit of measure, Gordon, has the following relationship with the signals from the detector channels: S[Gordon]=$-C_G$*ln(S) with the constant $C_G$=512/ln(1.25) ≈2994.487.

FIG. 5 shows, in line with FIG. 4, the graphically illustrated values for a correction table over the individual channels of the detector, but in this case the channels 161 to 167 and 321 to 336 for the exchanged modules have not been gauged, but rather have been calculated on the basis of the inventive method, to which end—as described above— the measured correction values for the old module in the current installation and in a reference installation and the measurement for the newly inserted module in a reference installation have also been used in accordance with an embodiment of the invention.

The result is that it can be seen that a virtually entire match in the characteristic curve profile of the correction values is discernable in the region of the table from 161 to 176 and from 321 to 336. This comparison thus shows that the inventive method can readily be used for recreating a correction table for the temperature dependencies of the detector signals, so as significantly to reduce the involvement when exchanging detector modules on a computed tomograph.

It goes without saying that the features of the invention which have been cited above can be used not just in the respective combination indicated but also in other combinations or on their own, without departing from the scope of the invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for exchanging a first detector module (m), including K channels (x) from k to j in an X-ray detector in a computed tomograph including a module configuration a with a total of M detector modules and K×M channels, for a second detector module (m'), wherein the first detector module includes an associated correction table ($T_{S(a,m,x)}$), for eliminating temperature-dependent signal changes, which is dependent on the respective module configuration of the detector and is recreatable following the exchange of a detector module, comprising:
    creating, for the first and second detector modules in a detector in a reference computed tomograph including the module configuration b, a respective correction table ($T_{S(b,m,x)}$, $T_{S(b,m',x)}$;
    ascertaining difference values in the correction tables; and
    calculating a new correction table ($T_{S(a,m',x)}$), for operating the second detector module (m') in the computed tomograph including the module configuration a, by transferring the ascertained difference values to the old correction table ($T_{S(a,m,x)}$).

2. The method as claimed in claim 1, wherein individual values for the new correction table ($T_{S(a,m'x)}$) are calculated on the following basis:

$$S_{a,m',x} = S_{b,m',x} + \frac{1}{K}\left(\sum_{i=k}^{j} S_{a,m,i} - \sum_{i=k}^{j} S_{b,m,i}\right)$$

where N is the number of channels of a detector module from channel k to j, $S_{n,o,p}$ corresponds to the correction value S for the module configuration n with the detector module o, and the channel x is an element of the channels k to j.

3. The method as claimed in claim 2, wherein, in the event of failure of a channel (i) of the detector module (m) which is to be exchanged, the signal values (S) for the channel are calculated by at least one of interpolating and extrapolating adjacent channels.

4. The method as claimed in claim 1, wherein, in the event of failure of a channel (i) of the detector module (m) which is to be exchanged, the signal values (S) for the channel are calculated by at least one of interpolating and extrapolating adjacent channels.

5. The method as claimed in claim 4, wherein a channel (i) is regarded as being faulty if the measured signal values (S) for the channel (i) exceed a prescribed limit value.

6. The method as claimed in claim 4, wherein the new correction table ($T_{S(a,m',x)}$) is created by reverting to a correction table ($T_{S(a,m,x)}$) measurement which was created and archived prior to failure.

7. The method as claimed in claim 4, wherein the new correction table ($T_{S(a,m',x)}$) is created by reverting to a correction table ($T_{S(b,m,x)}$) measurement which was created and archived prior to failure.

8. The method as claimed in claim 1, wherein a channel (i) is regarded as being faulty if the measured signal values (S) for the channel (i) exceed a prescribed limit value.

9. The method as claimed in claim 8, wherein the new correction table ($T_{S(a,m',x)}$) is created by reverting to a correction table ($T_{S(a,m,x)}$) measurement which was created and archived prior to failure.

10. The method as claimed in claim 8, wherein the new correction table ($T_{S(a,m',x)}$) is created by reverting to a correction table ($T_{S(b,m,x)}$) measurement which was created and archived prior to failure.

11. The method as claimed in claim 1, wherein the new correction table ($T_{S(a,m',x)}$) is created by reverting to a correction table ($T_{S(a,m,x)}$) measurement which was created and archived prior to failure.

12. The method as claimed in claim 11, wherein the new correction table $T_{S(a,m',x)}$ is created by reverting to a correction table ($T_{S(a,m,x)}$) measurement which was created and archived before the computed tomograph was delivered.

13. The method as claimed in claim 1, wherein the new correction table ($T_{S(a,m',x)}$) is created by reverting to a correction table ($T_{S(b,m,x)}$) measurement which was created and archived prior to failure, preferably before the computed tomograph was delivered.

14. The method as claimed in claim 13, wherein the new correction table ($T_{S(a,m',x)}$) is created by reverting to a correction table ($T_{S(b,m,x)}$) measurement which was created and archived before the computed tomograph was delivered.

15. The method as claimed in claim 1, wherein the first and second detector modules are at the same position.

16. The method as claimed in claim 1, wherein the differences in the correction tables are ascertained in an area of the channels of the detector module which is to be exchanged.

* * * * *